(12) United States Patent
Keyaki (10) Patent No.: US 9,691,166 B2
(45) Date of Patent: Jun. 27, 2017

(54) RADIATION CT APPARATUS

(71) Applicant: SHIMADZU CORPORATION, Kyoto (JP)

(72) Inventor: Yasuyuki Keyaki, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 385 days.

(21) Appl. No.: 14/536,043

(22) Filed: Nov. 7, 2014

(65) Prior Publication Data

US 2016/0133031 A1    May 12, 2016

(51) Int. Cl.
*G01N 23/04*    (2006.01)
*A61B 6/03*    (2006.01)
*G06T 11/00*    (2006.01)
*G01T 7/10*    (2006.01)
*A61B 6/00*    (2006.01)

(52) U.S. Cl.
CPC ............ *G06T 11/005* (2013.01); *A61B 6/032* (2013.01); *A61B 6/584* (2013.01); *G01N 23/046* (2013.01); *G01T 7/10* (2013.01); *G01N 2223/3035* (2013.01)

(58) Field of Classification Search
CPC .......... A61B 6/465; A61B 6/467; A61B 6/03; A61B 6/032; A61B 6/58; A61B 6/582; A61B 6/584; G01N 23/046; G01N 2223/303; G01N 2223/3035; G01N 2223/304
See application file for complete search history.

(56) References Cited

U.S. PATENT DOCUMENTS 6,434,214 B1 * 8/2002 Kawai .................... A61B 6/032
378/20
8,340,383 B2 * 12/2012 Matsuura ................. G06T 7/41
378/19

(Continued)

FOREIGN PATENT DOCUMENTS

JP    2005-37193 A    2/2005
JP    2007-333596 A    12/2007

OTHER PUBLICATIONS

Office Action dated Jul. 28, 2015, issued in counterpart Japanese application No. 2012-142037. (3 pages).

*Primary Examiner* — Thomas R Artman
(74) *Attorney, Agent, or Firm* — Westerman, Hattori, Daniels & Adrian, LLP (57) ABSTRACT

A radiation CT apparatus that can gain a clear tomogram without a rotation axis runout and without fail through a single CT scan and a simple operation is provided. When the data on the projection with radiation collected through a CT scan is first reconstructed through an arithmetic operation by a reconstruction arithmetic operation unit 13, temporary coordinates that have been set in advance as the coordinates of the projected rotation axis so as to construct a tomogram along a predetermined sliced surface are used, this tomogram is displayed on the screen for changing the rotation axis coordinates that include the temporary coordinates, and the coordinates of the projected rotation axis are shifted by any amount in any direction through an operation on the screen so that a reconstruction arithmetic operation is again carried out in the reconstruction arithmetic operation unit 13.

12 Claims, 8 Drawing Sheets

(56) References Cited

U.S. PATENT DOCUMENTS

2009/0046916 A1* 2/2009 Matsuura .................. G06T 7/41
  382/131
2016/0133031 A1* 5/2016 Keyaki ................ G06T 11/005
  378/20

* cited by examiner

RADIATION CT APPARATUS

BACKGROUND OF THE INVENTION

1. Field of the Invention

The present invention relates to a radiation CT apparatus for examining the internal structure or the existence of a defect of various types of industrial products in a non-destructive manner using radiation, for example, X-rays.

2. Description of Related Art

In industrial CT apparatuses, such a structure is generally used that a rotational table, on which an object to be examined is placed between a radiation source and a radiation detector that are provided so as to face each other, is provided so as to rotate around a rotation axis that is perpendicular to the direction of the axis of radiation (direction along the line that connects the radiation source and the radiation detector).

In such a radiation CT apparatus, a so-called CT scan is carried out in such a manner that the rotational table is rotated while the object is irradiated with radiation, and thus, radiation projection data of the object is collected by taking in the output of the radiation detector for each of the minute rotational angles of the rotational table. The data is used for the arithmetic operation of reconstruction so that a tomogram of the object along the sliced surface perpendicular to the rotation axis is constructed. Positional information on the coordinates of the rotation axis of the rotational table projected over the radiation detector is essential for this arithmetic operation of reconstruction.

Figure 6:
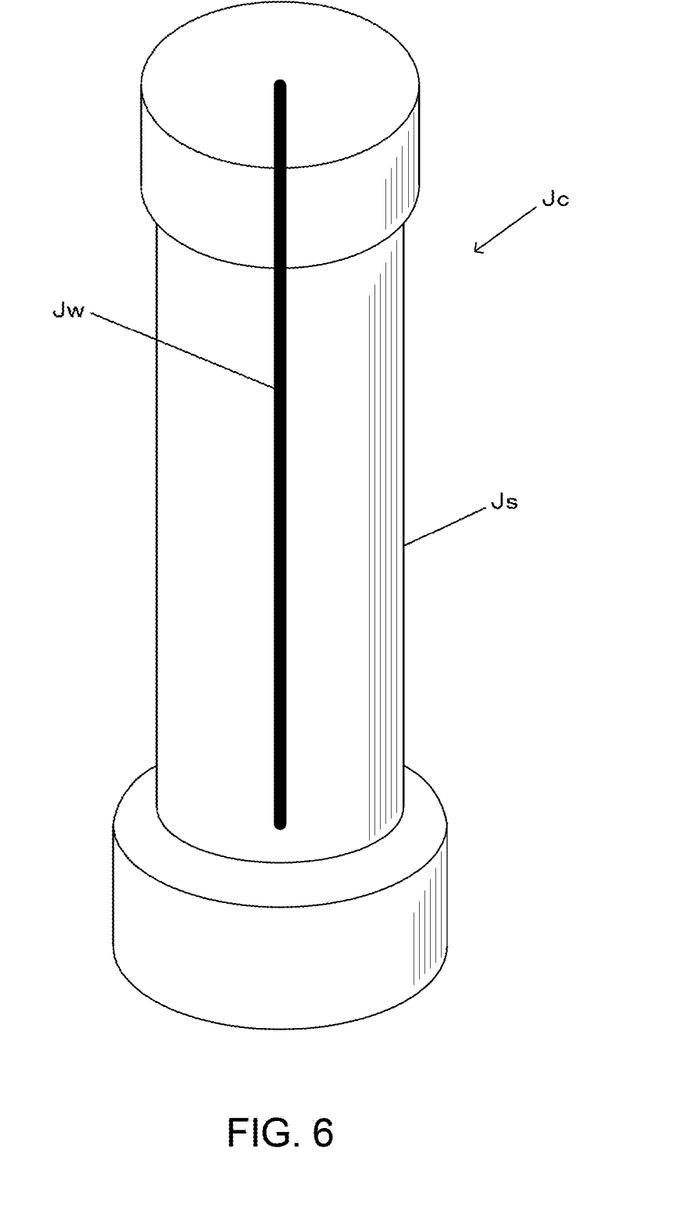
FIG. 6 is a perspective diagram for illustrating a phantom for calibrating the coordinates of the rotation axis projected over the radiation detector.

As a method for finding the coordinates of the rotation axis projected over the radiation detector, a method for using a phantom Jc for calibrating the position of the projected rotation axis as illustrated in FIG. 6 is generally used. This phantom Jc for calibrating the position of the projected rotation axis has such a structure that a wire Jw made of a material having a high absorbance of radiation, such as tungsten, is provided inside a support member Js made of a material that easily transmits radiation, such as acryl. The rotational table is irradiated with radiation from the source while rotating in such a state that this phantom Jc for calibrating the position of the projected rotation axis is placed on the rotational table, and thus, the output from the radiation detector is taken in so that the data on the projected wire Jw is collected. The coordinates of the rotation axis projected over the radiation detector can be found from the sinogram that is gained from the position of the projected pixel sequence along a plane that is perpendicular to the rotation axis included in the data on the projected wire Jw (see Patent Document 1). Whenever the positional relationship between the radiation source, the radiation detector, and the rotational table is changed, the correct values of the coordinates of the projected rotation axis are found according to the above-described method so that a tomogram without any blurring can be gained.

Another technique has been adopted as a method that is a simplified version of the above-described method. The coordinates of the rotation axis projected over the radiation detector were found in advance according to the above-described technique and stored for each of the multiple states when the neutral positional relationship between the radiation source, the radiation detector, and the rotational table were changed so that these multiple positional relationships and the coordinates of the projected rotation axis were used to find the coordinates of the projected rotation axis that correspond to the positional relationship between the radiation source, the radiation detector, and the rotational table when an image is taken through interpolation calculation or extrapolation calculation.

PRIOR ART DOCUMENT

Patent Document

Patent Document 1: Japanese Unexamined Patent Publication 2007-333596

SUMMARY OF THE INVENTION

1. Problem to Be Solved By the Invention

According to the former method for calculating the coordinates of the projected rotation axis using the above-described phantom for calibrating the position of the projected rotation axis, in some cases, the correct values of the coordinates of the projected rotation axis cannot be calculated due to the effects of the diameter of the tungsten wire Jw or the effects of the shift of the focal point of the radiation source during calibration, particularly when an image is taken with high magnification.

Likewise, according to the latter method for finding the coordinates of the projected rotation axis in advance from a number of positional relationships through interpolation or extrapolation, the correct values of the coordinates of the projected rotation axis cannot be found in the case where any one value of the coordinates of the projected rotation axis in the respective positional relationships that were found in advance includes an error in the same manner as described above. According to this method, in some cases, the time elapsed from the point in time when the coordinates of the projected rotation axis were found for a number of positional relationships also has an effect due to a chronological shift of the apparatus and the like.

Figure 7:
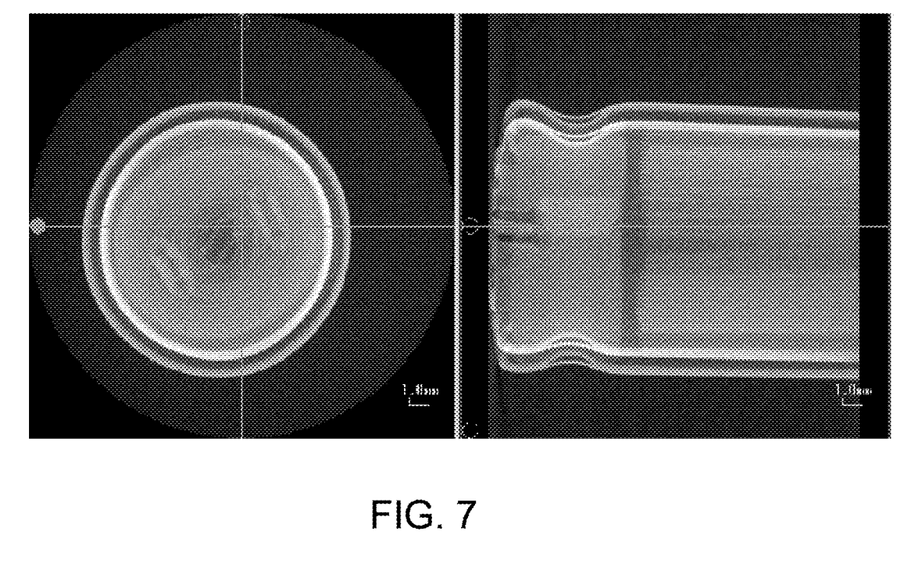
FIG. 7 is a pair of photographs showing an example of a tomogram with a rotation axis runout.
Figure 8:
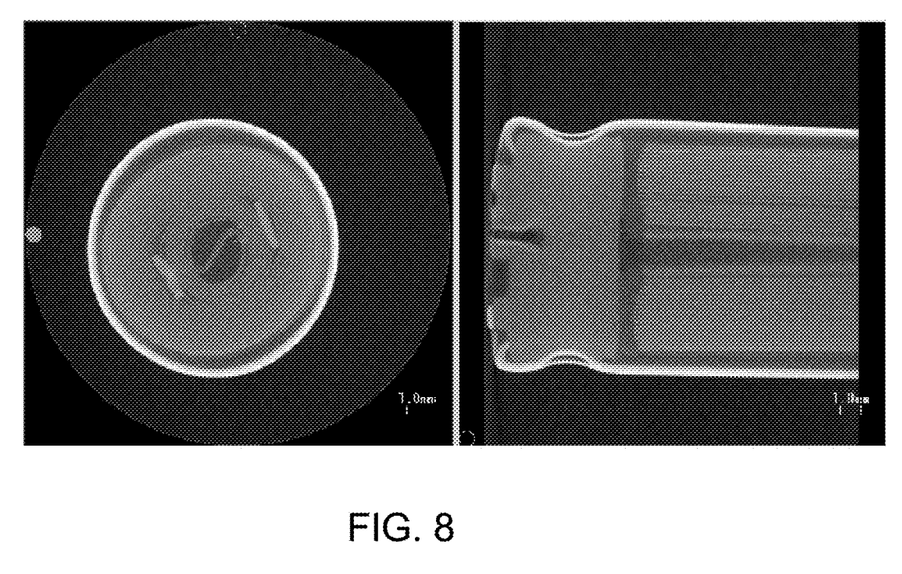
FIG. 8 is a pair of photographs showing an example of a tomogram without a rotation axis runout.

As described above, in the case where the correct values of the coordinates of the projected rotation axis cannot be found, a phenomenon that is referred to as "rotation axis runout" appears, where the tomogram that is found through the arithmetic operation of reconstruction becomes unclear due to a blurring of the tomogram in two directions perpendicular to each other as illustrated in FIG. 7. In the case where the correct values of the coordinates of the projected rotation axis are found, a tomogram as in FIG. 8 can be gained. In the case where such a rotation axis runout occurs, the coordinates of the projected rotation axis must be found through the calibration operation by again using the phantom for calibrating the rotation axis followed by the arithmetic operation of reconstruction by carrying out another CT scan, and thus, it is necessary to repeat these operations in a triangular manner until a tomogram with no rotation axis runout can be gained. In a cone-beam CT in particular, information on a three-dimensional tomogram made of a multiple number of tomograms is gained, and therefore, a lot of time and effort is wasted. In addition, the higher the magnification is at which the CT scan is carried out, the greater the effect the error between the original coordinates of the projected rotation axis and the coordinates found through the calculation has, and therefore, it is not easy to eliminate the rotation axis runout from the tomogram resulting from the arithmetic operation of reconstruction using the data gained through a CT scan with high magnification.

The present invention is provided in view of the above-described situation, and an object thereof is to provide a radiation CT apparatus that can gain a tomogram without a rotation axis runout and without fail through a single CT scan and a simple operation.

2. Means for Solving Problem

In order to achieve the above-described object, the radiation CT apparatus according to the present invention is a radiation CT apparatus having: a rotational table on which an object to be examined is placed, the rotational table being provided between a radiation source and a radiation detector, which are provided so as to face each other, so as to rotate around a rotation axis that is perpendicular to the direction of the radiation axis; and a reconstruction arithmetic operation means for constructing a tomogram of the object along a sliced surface that is perpendicular to the above-described rotation axis through an arithmetic operation using data of the projected object with radiation collected by taking in the output of the above-described radiation detector for each of the minute rotational angles gained when the rotational table is rotated while irradiating the object on the rotational table with radiation from the above-described radiation source, and is characterized in that the above-described reconstruction arithmetic operation means has: a screen display means for changing the rotation axis coordinates that constructs a tomogram along a predetermined sliced surface using temporary coordinates that have been set in advance as the coordinates of the above-described rotation axis projected over the above-described radiation detector in the first reconstruction arithmetic operation after collecting data on the above-described object projected with radiation, and at the same time displays a screen for changing the coordinates of the projected rotation axis that include the above-described tomogram and the temporary coordinates; and an instruction input means for instructing the above-described reconstruction arithmetic operation means to perform another arithmetic operation by shifting the coordinates of the projected rotation axis by any amount in any direction relative to the above-described temporary coordinates through an operation on the screen, wherein the above-described reconstruction arithmetic operation means carries out another reconstruction arithmetic operation by changing the coordinates of the projected rotation axis in accordance with the instructions (Claim 1).

Here, the present invention can adopt such a preferable configuration that the above-described radiation source generates radiation in a cone-beam form, the above-described radiation detector is a two-dimensional detector, and the above-described reconstruction arithmetic operation means constructs a number of tomograms along a number of sliced surfaces that are perpendicular to the above-described rotation axis through a reconstruction arithmetic operation, and at the same time carries out a first reconstruction arithmetic operation using the above-described temporary coordinates on one tomogram along a predetermined sliced surface and carries out the reconstruction arithmetic operation on the tomograms along the other sliced surfaces after receiving the instructions to that effect (Claim 2).

In addition, the present invention can adopt such a preferable configuration that: the above-described reconstruction arithmetic operation means carries out the first reconstruction arithmetic operation after collecting data on the above-described object projected with radiation as a reconstruction arithmetic operation for a tomogram using two coordinates that are shifted from the above-described temporary coordinates by a predetermined amount to the two sides with the temporary coordinates in between as the coordinates of the projected rotation axis together with a reconstruction arithmetic operation for a tomogram using the temporary coordinates; and the above-described screen display means for changing the rotation axis coordinates displays these three tomograms together with the coordinates of the projected rotation axis that are used for the respective arithmetic operations (Claim 3).

Furthermore, in the invention according to Claim 3, it is preferable for it to be possible to change the settings for the amount of shift from the above-described temporary coordinates of projection for the two coordinates that are shifted from the temporary coordinates to two sides with the temporary coordinates in between (Claim 4).

In addition, the present invention can adopt such a configuration that an image evaluation arithmetic operation means is further provided so as to find an evaluation value concerning the definition of each image through an arithmetic operation in terms of a tomogram gained through a reconstruction arithmetic operation using the above-described temporary coordinates, a tomogram gained through a reconstruction arithmetic operation using two coordinates that are shift from the temporary coordinates to the two sides by a predetermined amount with the temporary coordinates in between, and a tomogram gained through a reconstruction arithmetic operation according to an instruction by the above-described instruction input means, and the above-described screen display means for changing the rotation axis coordinates displays the evaluation values gained through arithmetic operations together with the respective tomograms (Claim 5).

Moreover, the present invention can also provide such a configuration that: a tomogram constructed through a reconstruction arithmetic operation using the above-described temporary coordinates and tomograms respectively constructed through a reconstruction arithmetic operation respectively using two projection coordinates that shift from the temporary coordinates to the two sides with the temporary coordinates in between are displayed on a display in such a state as to be aligned with the tomogram constructed through a reconstruction arithmetic operation using the above-described temporary coordinates in the center; and the above-described instruction input means is formed so as to give an instruction when either tomogram on the two sides is clicked, and at the same time, the direction of the shifting of the coordinates is set by clicking either tomogram, left or right, of the above-described tomograms on the two sides, and the amounts of shifting of the coordinates are respectively set in accordance with the distances of the click points on the above-described tomograms on the two sides from the center (Claim 6).

The above-described temporary coordinates used in the present invention may be any of the following coordinates (A) to (C): (A) coordinates calculated by using projection data collected when a phantom for calibrating the position of the projected rotation axis is placed on the above-described rotational table; (B) coordinates calculated through interpolation or extrapolation calculation from the projection coordinates in a positional relationship between the above-described radiation source, the radiation detector, and the rotational table when an image of the object is taken using a number of coordinates that have been calculated using projection data collected and stored when a phantom for calibrating the position of the projected rotation axis is placed on the above-described rotational table in each of the number of positional relationships between the above-described radiation source, the radiation detector, and the rotational table; and (C) designed coordinates that have been set from the beginning (Claim 7).

Meanwhile, Claims 8 to 11 relate to the invention according to which the rotation axis runout can be freely eliminated from the data of an object projected with radiation that has already been collected to construct a tomogram.

The invention according to Claim 8 provides a radiation CT apparatus having: a rotational table on which an object to be examined is placed, the rotational table being provided between a radiation source and a radiation detector, which are provided so as to face each other, so as to rotate around a rotation axis that is perpendicular to the direction of the radiation axis; and a reconstruction arithmetic operation means for constructing a tomogram of the object along a sliced surface that is perpendicular to the above-described rotation axis through an arithmetic operation using data of the projected object with radiation collected by taking in the output of the above-described radiation detector for each of the minute rotational angles gained when the rotational table is rotated while irradiating the object on the rotational table with radiation from the above-described radiation source, and is characterized by further having: a screen display means for changing the rotation axis coordinates which designates data on an object projected with radiation of which the tomogram is constructed through a reconstruction arithmetic operation, and thus displays a screen for changing the coordinates of the projected rotation axis that include the tomogram and the coordinates on the projected rotation axis using the construction of the tomogram; and an instruction input means for instructing the above-described reconstruction arithmetic operation means to carry out a second arithmetic operation by shifting the coordinates of the projected rotation axis by any amount and in any direction relative to the coordinates used for the construction of the above-described tomogram, wherein the above-described reconstruction arithmetic operation means changes the coordinates of the projected rotation axis in accordance with the instruction so as to carry out a second reconstruction arithmetic operation.

The invention according to Claim 8 can preferably adopt such a configuration that: the above-described reconstruction arithmetic operation means constructs tomograms through reconstruction arithmetic operations respectively using as the coordinates of the projected rotation axis the two coordinates shifting from the coordinates of the projected rotation axis used for the construction of a corresponding tomogram to the two sides by a predetermined amount respectively with the coordinates of the projected rotation axis in between when data on an object projected with radiation is designated to be displayed on the above-described screen display means for changing the rotation axis coordinates; and the above-described screen display means for changing the rotation axis coordinates displays these tomograms, including the above-described corresponding tomogram, together with the coordinates of the projected rotation axis used for the respective arithmetic operations (Claim 9).

In addition, in the invention according to Claim 9, it is preferable to adopt such a configuration that it is possible to change the setting of the respective amounts of shifting by which the two coordinates shift from the coordinates of the projected rotation axis used for the construction of the above-described corresponding tomogram to the two sides with the coordinates of the projected rotation axis in between (Claim 10).

Moreover, the inventions according to Claims 8 to 10 can preferably adopt such a structure that an image evaluation arithmetic operation means is further provided so as to find an evaluation value concerning the definition of each image through an arithmetic operation in terms of a tomogram displayed on the above-described screen for changing the coordinates of the projected rotation axis in accordance with the designation of the above-described data on projection with radiation, tomograms gained through a reconstruction operation using two coordinates shifting from the coordinates of the projected rotation axis used for the construction of the tomogram to the two sides by a predetermined amount respectively, and a tomogram gained through a reconstruction arithmetic operation in accordance with the instruction by the above-described instruction input means, and the above-described screen display means for changing the rotation axis coordinates displays the evaluation values gained through arithmetic operations together with the respective tomograms (Claim 11).

Furthermore, in the invention according to Claims 8 to 11, the tomogram that has already been constructed using the data on the projection with radiation designated to be displayed on the above-described screen display means for changing the rotation axis coordinates, and the tomograms respectively constructed through a reconstruction arithmetic operation using the two projection coordinates shifting from the coordinates of the projected rotation axis used for the construction of the tomogram to the two sides with the coordinates of the projected rotation axis in between are displayed on a display in such a state as to be aligned with the above-described tomogram that has already been constructed in the center; and the above-described instruction input means is formed so as to give an instruction when either tomogram on the two sides is clicked, and at the same time, the direction of the shifting of the coordinates is set by clicking either tomogram, left or right, of the above-described tomograms on the two sides, and the amounts of shifting of the coordinates are respectively set in accordance with the distances of the click points on the above-described tomograms on the two sides from the center (Claim 12).

The inventions according to Claims 1 to 7 are provided in order to achieve an object by using coordinates of a projected rotation axis as temporary coordinates to construct a tomogram of only a predetermined sliced surface through a reconstruction arithmetic operation instead of using a phantom for calibrating the rotation axis or using the coordinates of a projected rotation axis found in accordance with another method in order to carry out an immediate reconstruction arithmetic operation, and by displaying this information on a display so that an operator can change the coordinates of the rotation axis, and thus, the temporary coordinates of the projected rotation axis in which the displayed tomogram is found are shifted by any amount in any direction, making another reconstruction arithmetic operation possible when the operator judges so. At this time, the configuration allows an instruction to shift the coordinates to be given on the screen using the GUI (graphical user interface) function so that the operator can quickly and intuitively change the coordinates.

That is to say, the coordinates of the rotation axis projected over the radiation detector are found for setting in accordance with a certain method such as the use of a phantom for calibration so that the data of an object projected with radiation is collected, and after that, the reconstruction arithmetic operation means uses part of the collected data of projection and the coordinates of the projected rotation axis that have been set as described above so that a tomogram along a predetermined sliced surface (projection data of a mid-plane portion, for example) is constructed.

This tomogram is displayed on the display for changing the coordinates of the rotation axis, and at the same time, the above-described coordinates of the projected rotation axis are displayed as temporary coordinates. In addition, the reconstruction arithmetic operation means constructs a tomogram through a reconstruction arithmetic operation using the coordinates that have been shifted as the coordinates of the projected rotation axis when an instruction to shift the temporary coordinates by any amount in any direction on the above-described screen for changing the coordinates. Accordingly, the operator judges from the definition of the tomogram that has been displayed for the first time on the display for changing the coordinates whether or not the coordinates of the projected rotation axis should be changed or by how far and in which direction the coordinates should be shifted. The operator gives an instruction on the basis of this judgment so that a tomogram is displayed using the coordinates after being changed, and therefore, even if the original tomogram has a rotation axis runout, it can quickly be eliminated.

In the case of a cone-beam CT in particular, a reconstruction arithmetic operation is carried out only for a tomogram along a predetermined sliced surface such as a mid-plane using the temporary coordinates of the projected rotation axis so that this one tomogram is used to change the coordinates of the projected rotation axis to appropriate coordinates. After that, at the point in time when a clear tomogram without any rotation axis runout is gained, a reconstruction arithmetic operation is carried out on the remaining large number of tomograms, and therefore, the time required for eliminating the rotation axis runout can be shortened to a great extent as compared to the prior art, and the operation also becomes extremely simple.

As in the invention according to Claim 3, a tomogram gained through an arithmetic operation using the temporary coordinates of the projected rotation axis that have been set is displayed on the screen for changing the coordinates of the rotation axis in addition to the two tomograms gained through an arithmetic operation using the coordinates that are shifted by a predetermined amount to the two sides with the temporary coordinates in between so that the operator can quickly judge by how far and in which direction the coordinates should be shifted relative to the temporary coordinates so as to be used as the coordinates of the projected rotation axis in order to make the current tomograms in the temporary coordinates more defined.

In the case where an apparatus can find an evaluation value concerning the definition through an arithmetic operation such as the maximum brightness of each image in terms of the tomogram gained through an arithmetic operation using the temporary coordinates, the two tomograms gained through an arithmetic operation using the coordinates that are shifted from the temporary coordinates to the two sides, and the tomogram displayed on a display resulting from the reconstruction arithmetic operation after changing the coordinates, the time and effort required for the judgment by the operator for changing the coordinates can be reduced.

In the invention according to Claim 6, three tomograms in total, the tomogram gained by using the temporary coordinates in Claim 5 and the tomograms using the coordinates that are shifted from the temporary coordinates by a predetermined amount to the two sides, are displayed on the screen for changing the coordinates of the rotation axis in such a state that the three are aligned with the tomogram gained by using the temporary coordinates in the center so that either tomogram on the two sides can be clicked so as to input an instruction for the direction of the shifting of the coordinates and for the amount of shift in accordance with the distance from the center. This configuration allows the operator to quickly and intuitively give an instruction to shift the coordinates, which is effective in eliminating the rotation axis runout, and thus makes the system more convenient.

As in the invention according to Claim 7, the temporary coordinates used in the above-described inventions are coordinates of a projected rotation axis that are found each time it is necessary using a conventional phantom for calibrating the rotation axis or the coordinates of a projected rotation axis found from the coordinates of a projected rotation axis that had been found in advance through an interpolation or extrapolation calculation from a number of positional relationships between the radiation source, the radiation detector, and the rotational table respectively, and in addition can be the coordinates of a projected rotation axis for designing an apparatus because a reconstruction arithmetic operation is carried out by freely shifting the coordinates in each of the above-described inventions.

In each of the inventions according to Claims 8 to 11, the coordinates of the projected rotation axis are shifted in order to carry out reconstruction as a result of the judgment by the operator so that the above-described technology for gaining a tomogram without the rotation axis runout is applied to the projection data from which a tomogram has already been gained through a reconstruction arithmetic operation.

That is to say, a corresponding tomogram and the coordinates of the projected rotation axis that are used for the reconstruction arithmetic operation to gain the tomogram are displayed on the screen for changing the coordinates of the rotation axis by calling out the projection data of an object of which the tomogram has already been constructed through a reconstruction arithmetic operation. On this screen, the coordinates of the projected rotation axis are shifted by means of an instruction input means so that the coordinates after shifting are used as the coordinates of the projected rotation axis, and a new tomogram is again reconstructed from the projection data of the object and displayed. The operator gives an instruction to shift the coordinates of the projected rotation axis when a rotation axis runout is perceived in the original tomogram so that the rotation axis runout can be eliminated.

In the invention according to Claim 9, the tomogram that has already been constructed from the projection data that has been called out in the same manner as in the above and the two tomograms that have been constructed through a reconstruction arithmetic operation from the projection data of an object using the coordinates that have been shifted by a predetermined amount to the two sides of the coordinates of the projected rotation axis used for the reconstruction of the tomogram are displayed together with the coordinates of the projected rotation axis used for the reconstruction of the respective tomograms. As a result, in the same manner as in the invention according to Claim 3, the operator can quickly judge by how far and in which direction the coordinates of the projected rotation axis should be shifted from the coordinates of the projected rotation axis used for the reconstruction of the tomogram that has already been constructed in order to gain the coordinates to be used to make the tomogram more defined than the current tomogram.

In the inventions according to Claims 8 to 10, when the invention according to Claim 11 is applied, an evaluation value concerning the definition in terms of each tomogram is displayed in the same manner as in the invention according to Claim 5 so that it is useful for the judgment of the operator when the coordinates of the projected rotation axis are changed. In addition, when the invention according to Claim 12 is applied, the same working effects as in the invention according to Claim 6 can be expected.

3. Effects of the Invention

The inventions according to Claims 1 to 7 allow the projection data gained from the CT scan (collection of data on the object projected with radiation) to be provided to a reconstruction arithmetic operation where the temporary coordinates that are set in advance are used as the coordinates of the projected rotation axis so that a tomogram along a predetermined sliced surface such as a mid-plane is constructed and displayed on the screen for changing the coordinates of the rotation axis together with the temporary coordinates used at that time. When the change of the coordinates of the projected rotation axis is instructed on this screen, a tomogram is constructed through a reconstruction arithmetic operation using the new coordinates after the change as the coordinates of the projected rotation axis and displayed, and therefore, a tomogram without a rotation axis runout can be gained through a simple operation.

In a comb-beam CT in particular, only a tomogram along a predetermined sliced surface such as a mid-plane is constructed using temporary coordinates, whereas tomograms along other sliced surfaces are reconstructed after the rotation axis runout has been removed by changing the coordinates of the projected rotation axis on the basis of the tomogram gained by using the temporary coordinates, and therefore, information on the definitive three-dimensional tomograms without a rotation axis runout can be gained through an effective and quick operation. In addition, a definitive tomogram without a rotation axis runout can be gained through a simple operation from CT scans with high magnification, from which it has been difficult to gain a definitive tomogram according to the prior art.

In the inventions according to Claims 8 to 12, the projection data on CT scans from which a tomogram has already been reconstructed can be designated so that the coordinates of the projected rotation axis used for the reconstruction arithmetic operation can be freely changed so as to gain tomograms through other reconstruction arithmetic operations, and therefore, even in the case where the coordinates of the projected rotation axis used for the first reconstruction arithmetic operation are not precise coordinates, definitive tomograms without a rotation axis runout can be gained through the subsequent simple operations.

DETAILED DESCRIPTION OF EMBODIMENTS

In the following, the embodiments of the present invention are described in reference to the drawings.

Figure 1:
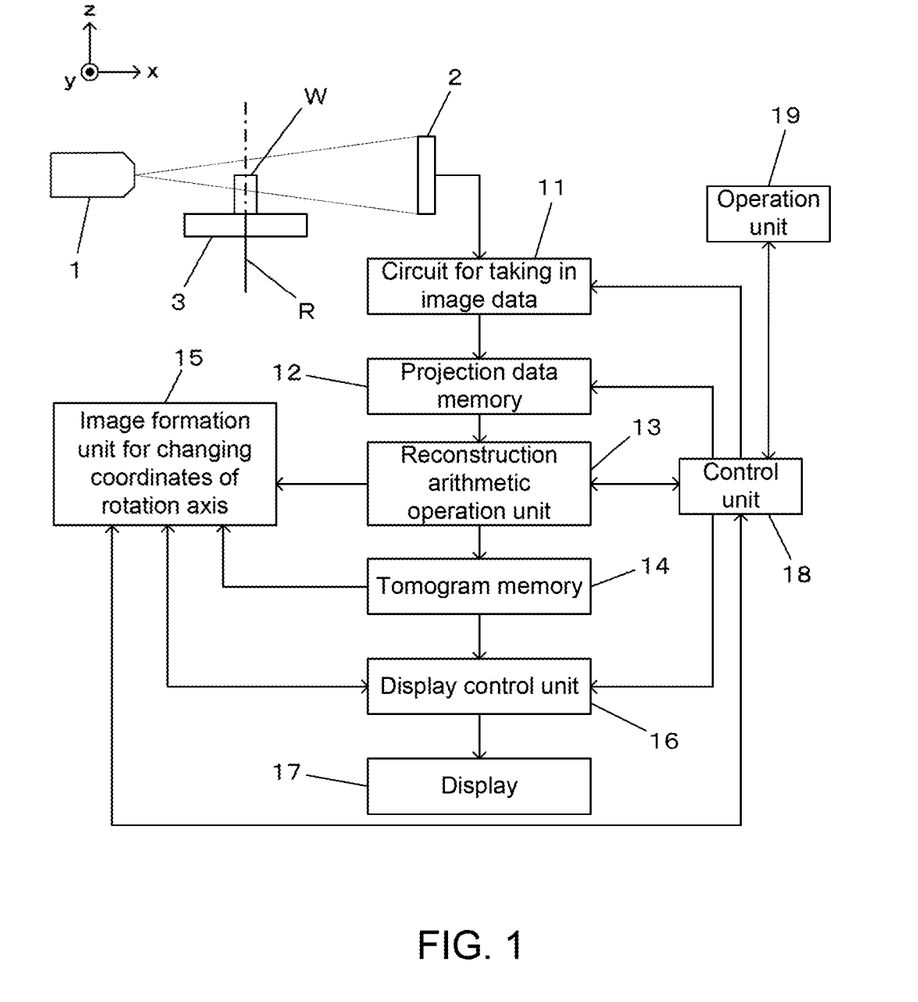
FIG. 1 is a diagram showing the mechanical configuration and the functional configuration together according to the present invention.

FIG. 1 is a diagram showing the structure of an embodiment of the present invention and consisting of the mechanical configuration and the functional configuration.

In this embodiment, the radiation source 1 is provided so as to generate radiation in cone-beam form in the lateral direction (direction of the X axis), a two-dimensional radiation detector 2 is provided so as to face the radiation source 1, and a rotational table 3 is provided between these. The radiation source 1 is typically an X-ray tube that generates X-rays as radiation. In addition, the radiation detector 2 is typically a flat panel type X-ray detector.

The rotational table 3 rotates around the rotation axis R along the vertical direction (direction of the Z axis) perpendicular to the direction of radiation along the direction of the X axis along the line connecting the radiation source 1 and the radiation detector 2. The rotational table 3 can be shifted in the direction of radiation by driving the table shifting mechanism (not shown), and the magnification of a CT scan can be changed as a result of this shift. In addition, the radiation detector 2 can be shifted in the direction of radiation by driving the detector shifting mechanism (not shown).

At the time of CT scanning, the rotational table 3 is rotated in such a state that an object W is placed on the rotational table 3 while being irradiated with radiation from the radiation source 1, and the output from the radiation detector is taken into a circuit for taking in image data 11 by each of the predetermined minute rotational angles. The data that has been taken in is stored in a projection data memory 12 as the data of the object projected with radiation. The data stored in the projection data memory 12 is provided for a reconstruction arithmetic operation by a reconstruction arithmetic operation unit 13. The reconstruction arithmetic operation unit 13 reconstructs the projection data stored in the projection data memory 12 through a publicly-known algorithm such as a reverse projection method or the like using the coordinates of the rotation axis R of the rotational table 3 projected over the radiation detector 2 (Y axis coordinates) that have been found by using a phantom for calibrating the rotation axis in advance, and thus, information on the three-dimensional tomograms of the object W is gained, in other words, the respective tomograms along a large number of sliced surfaces are constructed. The results of this reconstruction arithmetic operation are stored in a tomogram memory 14.

A screen formation unit for changing coordinates of the rotation axis 15 forms a screen for changing the coordinates of the rotation axis displayed after the completion of CT scanning when the center adjustment function for changing the below-described coordinates of the projected rotation axis is activated. A screen formed by the screen formation unit for changing the coordinates of the rotation axis 15 includes three tomograms, including a tomogram along a mid-plane that has been constructed through a reconstruction arithmetic operation using temporary coordinates in the below-described reconstruction arithmetic operation unit 13, and changing the coordinates of the projected rotation axis can be instructed on this screen. This screen for changing the coordinates of the rotation axis is displayed on a display 17 through a display control unit 16. In addition, tomograms stored in the above-described tomogram memory 14 can be freely displayed on the display 17 through the display control unit 16 by giving an instruction.

The above-described circuit for taking in image data 11, the projection data memory 12, the reconstruction arithmetic operation unit 13, the tomogram memory 14, the screen formation unit for changing the coordinates of the rotation axis 15, the display control unit 16, and the display 17 are placed under the control of the control unit 18. An operation unit 19 consisting of a keyboard, a mouse, a joystick, and the like for giving various types of instructions and settings to the apparatus is connected to the control unit 18. Here, the control unit 18 and the like shown in FIG. 1 as a box are actually formed of a computer and its peripheral device so that a function following the installed program can be implemented. However, FIG. 1 shows the main functions in boxes for the convenience of the description.

This embodiment is characterized by having a center adjustment function where a reconstruction arithmetic operation is carried out by freely changing the coordinates of the projected rotation axis. This center adjustment function can be activated in either case where a selection is made prior to CT scanning or it is desired to obtain a tomogram without a rotation axis runout from the radiation projection data where the CT scan has already been completed.

Figure 2:
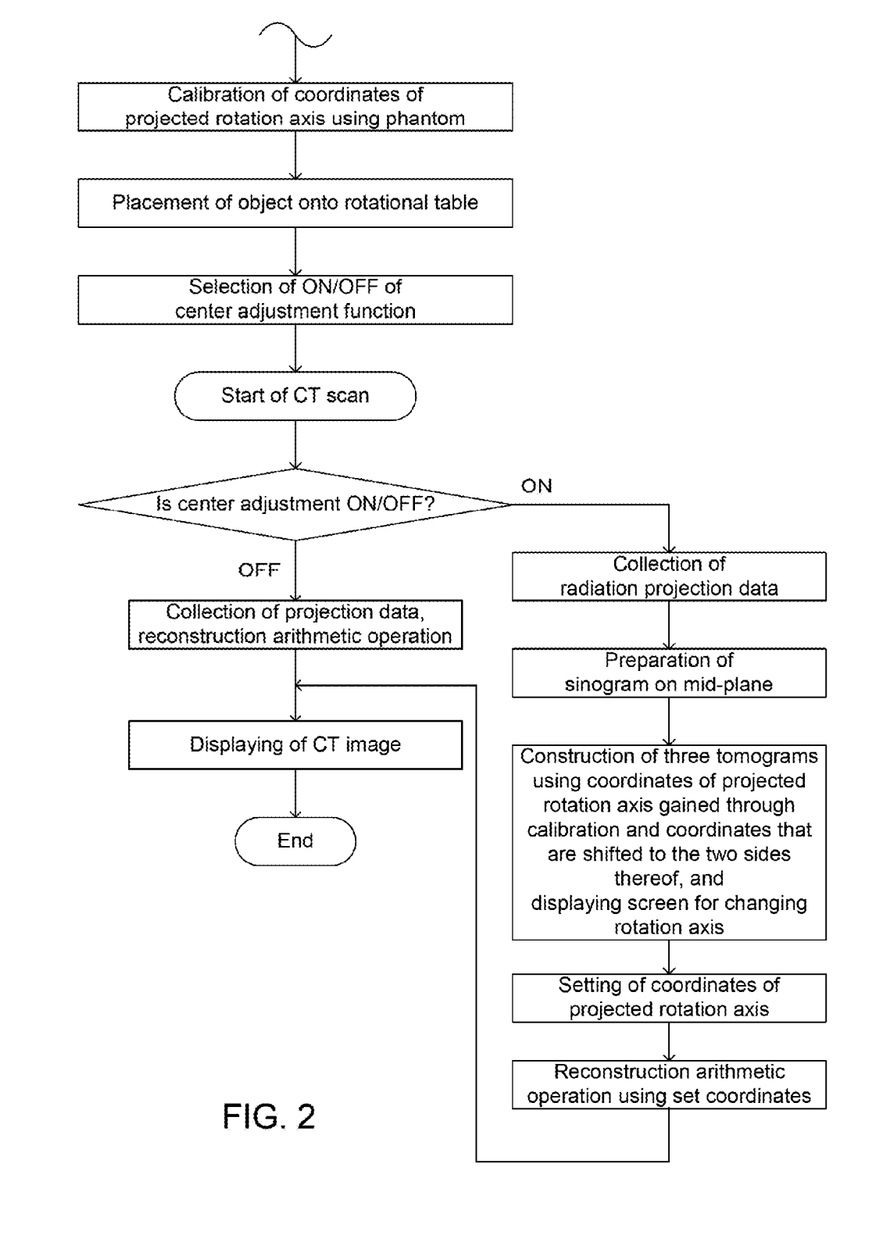
FIG. 2 is a flow chart showing the operational procedure when CT scanning is carried out according to an embodiment of the present invention.

First, the procedure is described in the case where CT scanning is carried out. FIG. 2 is a flow chart showing a procedure when CT scanning is carried out. In the case of CT scanning, the coordinates of the projected rotation axis are calculated on the basis of the projection data that has been adopted using a phantom for calibrating the rotation axis in the same manner as in the prior art and are set in the reconstruction arithmetic operation unit 13. In addition, whether or not the center adjustment function is used can be selected through ON/OFF or the like in the check box prior to the start of the CT scan after an object has been placed on the rotational table.

In the case where the center adjustment function is not selected, the data of an object projected with radiation is collected by carrying out CT scanning in the same manner as in the prior art, and together with this, a reconstruction arithmetic operation is carried out using this data, and thus, information on the three-dimensional tomograms of the object is gained.

In the case where the center adjustment function is selected, the data of an object projected with radiation is collected, and at this time, no reconstruction arithmetic operation is carried out, but a sinogram on a mid-plane is prepared (sampled). After the completion of the CT scan, the coordinates of the projected rotation axis that are found in advance and set in the reconstruction arithmetic operation unit 13 are used as temporary coordinates so that a reconstruction arithmetic operation is carried out on the sinogram on the mid-plane and a tomogram is constructed. In addition, the same sinogram is used to construct respective tomograms through a reconstruction arithmetic operation where the coordinates gained by shifting the temporary coordinates by a predetermined amount to the two sides in the direction of the Y axis are used as the coordinates of the projected rotation axis. These three tomograms are displayed on the screen for changing the coordinates of the rotation axis on the basis of the GUI technology together with the coordinates of the projected rotation axis used for the respective reconstructions. The operator can freely change the coordinates of the projected rotation axis as shown below while checking this screen so that a tomogram without a rotation axis runout is gained. After that, the reconstruction arithmetic operation unit 13 constructs information on the three-dimensional tomograms of the object through a reconstruction arithmetic operation using the coordinates of the projected rotation axis after changing and using all the data stored in the projection data storage unit 12 by giving an instruction to the effect that the selection is completed.

Figure 3:
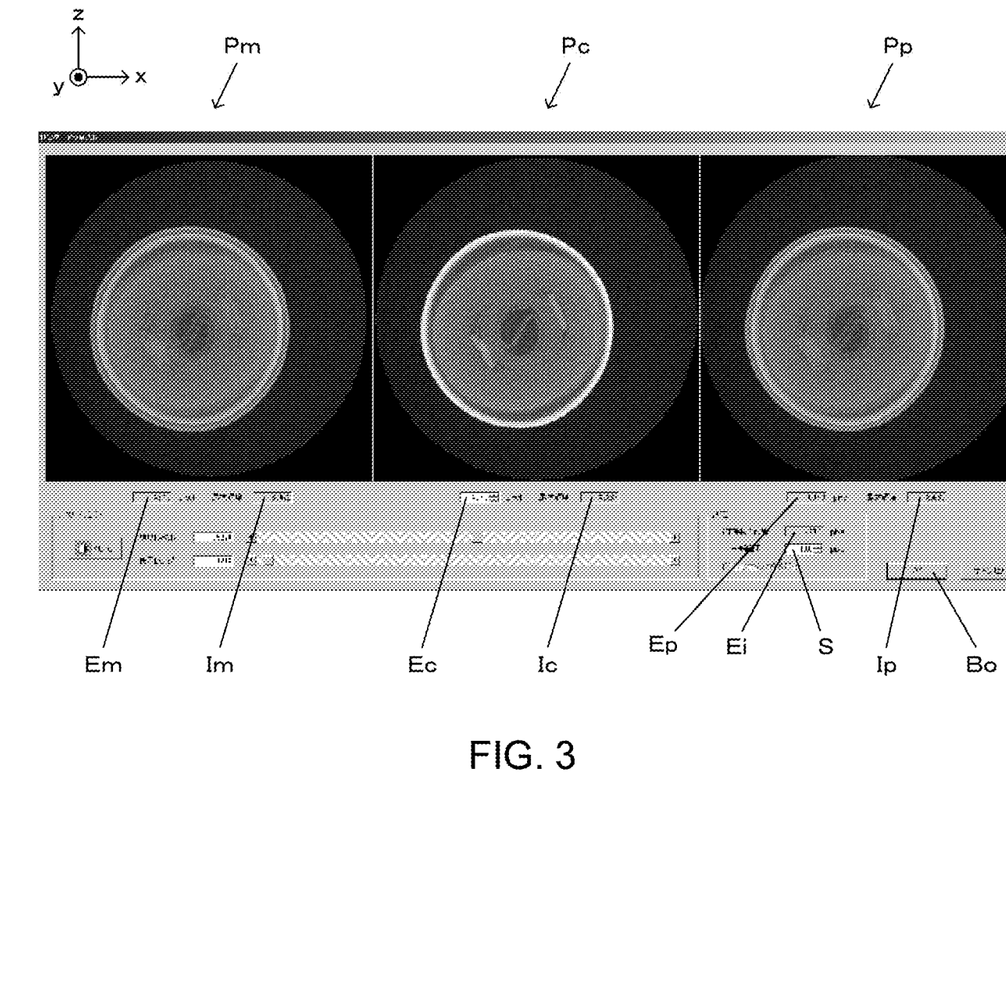
FIG. 3 is a diagram illustrating a screen for changing the coordinates of the rotational axis according to an embodiment of the present invention.

FIG. 3 shows an example of a screen for changing the coordinates of a rotation axis. In FIG. 3, the tomogram Pc is a tomogram constructed through a reconstruction arithmetic operation using coordinates of the projected rotation axis found on the basis of data gained using a phantom, that is to say, using temporary coordinates. The tomogram Pm in the figure is a tomogram constructed through a reconstruction arithmetic operation using the coordinates that are shifted from the temporary coordinates by a predetermined amount, for example, by five pixels, in one direction along the Y axis (towards the minus side, for example) as the coordinates of the projected rotation axis. In addition, the tomogram Pp is a tomogram constructed through a reconstruction arithmetic operation using the coordinates that are shifted from the temporary coordinates by the predetermined amount in the direction along the Y axis opposite that in Pm (towards the plus side, for example) as the coordinates of the projected rotation axis. Beneath these tomograms Pc, Pm, and Pp, display portions Ec, Em, and Ep of the coordinates of the projected rotation axis (coordinates along Y axis, pixel display) used for the respective reconstruction arithmetic operations and display units Ic, Im, and Ip of the maximum brightness of the respective tomograms Pc, Pm, and Pp are provided.

Thus, an instruction to change the coordinates of the projected rotation axis can be given as shown below on this screen for changing the coordinates of the rotation axis.

By clicking with the mouse the tomogram on the left or on the right from among the three tomograms, the coordinates of the projected rotation axis change in the corresponding direction. That is to say, the coordinates of the projected rotation axes Em, Ec, and Ep move towards the minus side, linking the clicking of the tomogram Pm on the left side, and move towards the plus side, linking the clicking of the tomogram Pp on the right side. At the same time as such a change in the coordinate values, the reconstruction arithmetic operation unit 13 carries out a reconstruction arithmetic operation on the mid-plane using the coordinate values after the change as the coordinates of the projected rotation axis, and thus, the tomograms Pm, Pc, and Pp also change to the new images through reconstruction arithmetic operations respectively. Together with this, the values displayed on the maximum brightness displaying units Im, Ic, and Ip for the respective tomograms Pm, Pc, and Pp also change.

It can be judged that the coordinates Ec used for the reconstruction of the tomogram Pc at the center to be the optimal coordinates of the projected rotation axis at the point in time when such a state is gained that the tomogram Pc at the center is clear and the rotation axis runouts occur in the tomograms Pm and Pp on both sides approximately equally, or at the point in time when such a state is gained that the maximum brightness value Ic corresponding to the tomogram Pc at the center becomes maximum from among the maximum brightness values displayed so as to correspond to the respective tomograms Pm, Pc, and Pp and the maximum brightness values Im and Ip of the tomograms Pm and Pp on both sides are values equally lower than that of Ic on the above-described screen for changing the coordinates of the rotation axis. After the above-described judgment, the "OK" button Bo is clicked on the screen so that information on the three-dimensional tomograms of the object, that is to say, the tomograms along all of the sliced surfaces, is constructed using the entirety of the data stored in the projection data memory 12 through a reconstruction arithmetic operation using the above-described optimal coordinates of the projected rotation axis.

During the above-described operational procedure in the present invention, a tomogram without a rotation axis runout can be intuitively selected while viewing the three tomograms that have been gained through a reconstruction arithmetic operation respectively using the three sets of coordinates that are shifted from each other by a predetermined amount as the coordinates of the projected rotation axis to be used for a reconstruction arithmetic operation. In addition, the maximum brightness values of the tomograms are also displayed in such a manner that these maximum brightness values are low in the case where there is a rotation axis runout in the tomogram, and thus are useful as an evaluation value of the definition of the image. It is also possible to select the optimal coordinates of the projected rotation axis in reference to these maximum brightness values, and in this case, the optimal coordinates of the projected rotation axis can be easily set without requiring skill or experience.

Here, on the screen in FIG. 3, the values of the original coordinates of the projected rotation axis Ec used for the reconstruction of the tomogram Pc at the center displayed on the original screen are displayed in the coordinate initial value display unit Ei, and therefore, the screen can be returned to the original screen even after various changes in the coordinates.

In addition, the amount by which the coordinates of the projected rotation axis Em and Ep are shifted from Ec for the reconstruction of the tomograms Pm and Pp displayed on the two sides of the tomogram Pc at the center can be changed in the setting unit S in FIG. 3 so that the amount of shift can be freely changed to an appropriate amount for finding the optimal coordinates of the projected rotation axis in accordance with the form and the type of object.

Figure 4:
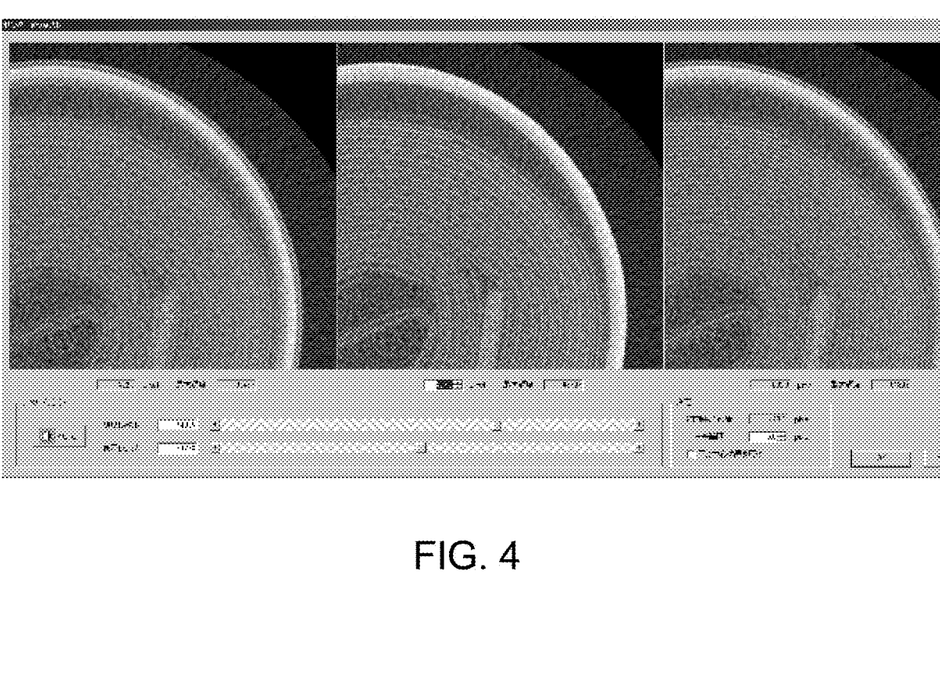
FIG. 4 is a diagram showing a state where a magnification of a tomogram is displayed on a screen for changing the coordinates of the rotation axis according to an embodiment of the present invention.

Furthermore, a magnification of each of the three tomograms Pm, Pc, and Pp can be displayed in a digital zooming manner by scrolling upwards with the mouse when the cursor is placed on the tomogram on the screen in FIG. 3, and at the same time, the location of the magnified image on the display can be changed by dragging the cursor that is placed on the tomogram Pc at the center. FIG. 4 shows an example of an enlarged tomogram displayed in this manner. This function can be used to make intuitive judgment easy when a magnification of an outline portion that is easily affected by a rotation axis runout due to the shape of the object is displayed.

Furthermore, the tomogram on the left or on the right can be clicked with the mouse so that the coordinates of the projected rotation axis change in the corresponding direction where the amount by which the coordinates shift by one click changes in the configuration. That is to say, when a location in the half of the tomogram Pm or Pp on the left or on the right on the side closer to the tomogram Pc at the center is clicked, the image shifts by 1.0 pixel, and when a location in the half of the tomogram Pm or Pp on the left or on the right on the side away from the tomogram Pc at the center is clicked, the image shifts by 5.0 pixels. The clicked point can be changed appropriately in accordance with the degree of the rotation axis runout of the tomogram so that a quick change in the coordinates and precise setting become possible.

Figure 5:
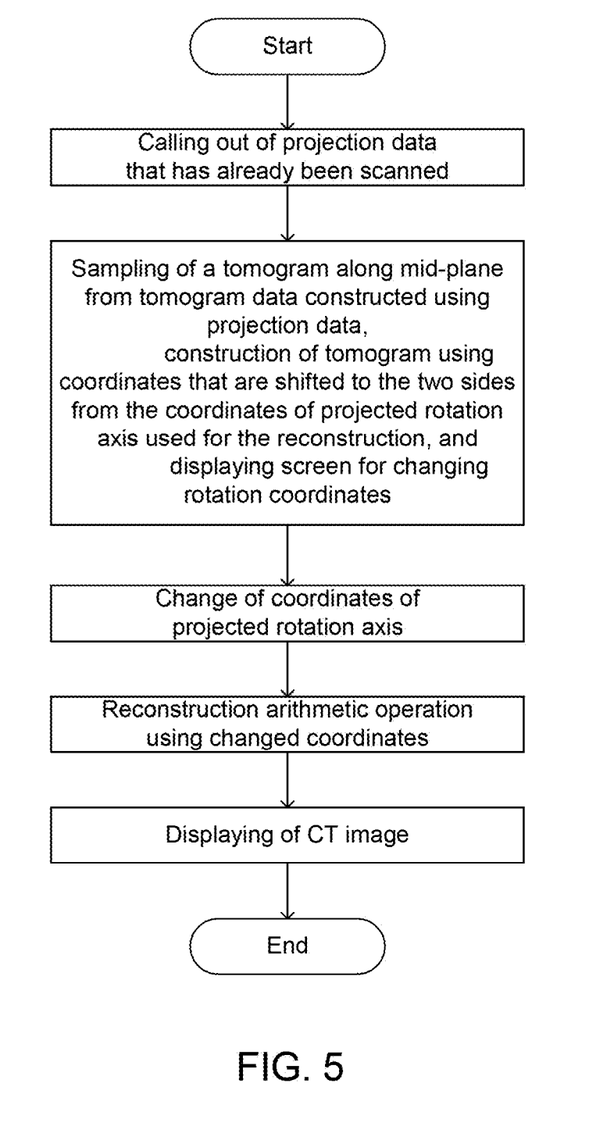
FIG. 5 is a flow chart showing the operational procedure where the coordinates of the rotation axis are changed using the projection data of the CT scans so as to again carry out a reconstruction arithmetic operation.

Though examples of the functions and the operations are shown in the case where the center adjustment function is activated prior to CT scanning in the above, the center adjustment function can be activated for the data after the completion of a reconstruction arithmetic operation after CT scanning so that the tomogram can be changed to a more definitive tomogram without a rotation axis runout according to this embodiment. FIG. 5 shows a flow chart of the procedure for this case.

When an instruction is given for center adjustment of the data after scanning, a screen for changing the coordinates of the rotation axis that includes three tomograms is displayed in the same manner as in FIG. 3. Here, the tomogram Pc at the center from among the three tomograms on this screen for changing the coordinates of the rotation axis at the time of the center adjustment of the data after scanning is a tomogram along the mid-plane that has already been constructed through a reconstruction arithmetic operation where the coordinates of the projected rotation axis are coordinates of the projected rotation axis actually used for the reconstruction arithmetic operation, and the coordinates thereof are displayed in the display unit Ec of the coordinates of the projected rotation axis provided beneath the tomogram Pc in the same manner as in the above. In addition, the tomograms Pm and Pp displayed on the two sides thereof are tomograms gained through a new reconstruction arithmetic operation for the projection data of the mid-plane using the coordinates shifting by a predetermined amount in the directions opposite each other from the coordinates of the projected rotation axis displayed in the above as Ec, and the coordinates of the projected rotation axis respectively used for gaining the tomograms are displayed in the corresponding display units Em and Ep. In addition, the maximum brightness of the respective tomograms Pm, Pc, and Pp are displayed in the corresponding display units Im, Ic, and Ip in the same manner as above.

Such a screen for changing the coordinates of the rotation axis is used to change the optimal coordinates of the projected rotation axis through the same procedure as described above where the "OK" button Bo is clicked on the screen so that information on the three-dimensional tomograms of the object can be constructed through another reconstruction arithmetic operation for the entirety of the projection data using the coordinates of the projected rotation axis after the change.

The above-described center adjustment function for the data after scanning can be used to make it possible to change the tomogram that has already been gained to a more definitive tomogram with the rotation axis runout being eliminated.

Though in the above-described embodiment the maximum brightness values of the images are used as evaluation values for evaluating the definition of the tomograms, other publicly-known evaluation values for the definition used in various types of image processes, for example, values gained by collecting differential values of the brightness in parts of images, can be used as the evaluation value for the definition.

EXPLANATION OF SYMBOLS

1 Radiation source
2 Radiation detector
3 Rotational table

11 Circuit for taking in image data
12 Projection data memory
13 Reconstruction arithmetic operation unit
14 Tomogram memory
15 Screen formation unit for changing coordinates of rotation axis
16 Display control unit
17 Display
18 Control unit
19 Operation unit

What is claimed is:

1. A radiation CT apparatus, comprising: a rotational table on which an object to be examined is placed, a radiation source, and a radiation detector, the rotational table being provided between the radiation source and the radiation detector, which are provided so as to face each other, and so as to rotate around a rotation axis that is perpendicular to the direction of the radiation axis; and a reconstruction arithmetic operation means configured to construct a tomogram of the object along a sliced surface that is perpendicular to said rotation axis through a first reconstruction arithmetic operation using data of the projected object with radiation collected by taking in the output of said radiation detector for each of the minute rotational angles gained when the rotational table is rotated while irradiating the object on the rotational table with radiation from said radiation source, wherein said reconstruction arithmetic operation means comprises: (1) a screen display for changing the rotation axis coordinates that constructs a tomogram along a predetermined sliced surface using temporary coordinates that have been set in advance as the coordinates of said rotation axis projected over said radiation detector in the first reconstruction arithmetic operation after collecting data on said object projected with radiation, and at the same time displays a screen for changing the coordinates of the projected rotation axis that include said tomogram and the temporary coordinates; and (2) an instruction input means for instructing said reconstruction arithmetic operation means to perform a second reconstruction arithmetic operation by shifting the coordinates of the projected rotation axis by any amount in any direction relative to said temporary coordinates through an operation on the screen, wherein said reconstruction arithmetic operation means is configured to carry out the second reconstruction arithmetic operation by changing the coordinates of the projected rotation axis in accordance with the instructions, and said screen display means for changing the rotation axis coordinates allows three tomograms in total to be displayed on a display in such a state as to be aligned with the center one constructed through a reconstruction arithmetic operation using said temporary coordinates, and the remaining two respectively constructed through a reconstruction arithmetic operation respectively using two projection coordinates that shift from the temporary coordinates to the two sides by a predetermined amount with the temporary coordinates in between.

2. The radiation CT apparatus according to claim 1, wherein said radiation source is configured to generate radiation in a cone-beam form, wherein said radiation detector is a two-dimensional detector, and wherein said reconstruction arithmetic operation means constructs a plurality of tomograms along a plurality of sliced surfaces that are perpendicular to said rotation axis through a reconstruction arithmetic operation, and at the same time carries out the first reconstruction arithmetic operation using said temporary coordinates on one tomogram along a predetermined sliced surface and carries out the reconstruction arithmetic operation on the tomograms along the other sliced surfaces after receiving the instructions to that effect.

3. The radiation CT apparatus according to claim 1, wherein said reconstruction arithmetic operation means is configured to carry out arithmetic operations on said there tomograms together; and wherein said screen display for changing the rotation axis coordinates is configures to display the three tomograms and the coordinates of the projected rotation axis that are used for the respective arithmetic operations.

4. The radiation CT apparatus according to claim 3, wherein it is possible to change the settings for said predetermined amount in terms of the shifting of the projection coordinates of said rotation axis.

5. The radiation CT apparatus according to claim 1, further comprising an image evaluation arithmetic operation means configured to an evaluation value concerning the definition of each image through an arithmetic operation in terms of said three tomograms.

6. The radiation CT apparatus according to claim 1, wherein the apparatus is configured so that said instruction input means is configured to give an instruction when either tomogram on the two sides from among said three tomograms is clicked, and at the same time, the direction of the shifting of the coordinates is set by clicking either tomogram, left or right, of said tomograms on the two sides, and the amounts of shifting of the coordinates are respectively set in accordance with the distances of the click points on said tomograms on the two sides from the center.

7. The radiation CT apparatus according to claim 1, wherein said temporary coordinates are any of the following coordinates (A) to (C):

(A) coordinates calculated by using projection data collected when a phantom for calibrating the position of the projected rotation axis is placed on said rotational table;

(B) coordinates calculated through interpolation or extrapolation calculation from the projection coordinates in a positional relationship between said radiation source, the radiation detector, and the rotational table when an image of the object is taken using a number of coordinates that have been calculated using projection data collected and stored when a phantom for calibrating 10 the position of the projected rotation axis is placed on said rotational table in each of the number of positional relationships between said radiation source, the radiation detector, and the rotational table; and (C) designed coordinates that have been set from the beginning.

8. A radiation CT apparatus, comprising: a rotational table on which an object to be examined is placed, a radiation source, and a radiation detector, the rotational table being provided between the radiation source and the radiation detector, which are provided so as to face each other, and so as to rotate around a rotation axis that is perpendicular to the direction of the radiation axis; and a reconstruction arithmetic operation means configured to a tomogram of the object along a sliced surface that is perpendicular to said rotation axis through a first reconstruction arithmetic operation using data of the projected object with radiation collected by taking in the output of said radiation detector for each of the minute rotational angles gained when the rotational table is rotated while irradiating the object on the rotational table with radiation from said radiation source, further comprising: (1) a screen display means for changing the rotation axis coordinates which designates data on an object projected with radiation of which the tomogram is constructed through a reconstruction arithmetic operation, and thus displays a screen for changing the coordinates of the projected rotation axis that include the tomogram and the coordinates on the projected rotation axis using the construction of the tomogram; and (2) an instruction input means for instructing said reconstruction arithmetic operation means to carry out a second arithmetic operation by shifting the coordinates of the projected rotation axis by any amount and in any direction relative to the coordinates used for the construction of said tomogram, wherein said reconstruction arithmetic operation means changes the coordinates of the projected rotation axis in accordance with the instruction so as to carry out a second reconstruction arithmetic operation, and said screen display means for changing the rotation axis coordinates allows three tomograms in total to be displayed on a display in such a state as to be aligned with the center one displayed on said screen for changing the coordinates o the projected rotation axis in accordance with the designation of said data on projection with radiation, and the remaining two constructed though reconstruction operations respectively using two coordinates shifting from the coordinates of the projected rotation axis in accordance with the designation of said data on projection with radiation, and the remaining two constructed through reconstruction operations respectively suing two coordinates shifting from the coordinates of the projected rotation axis used for the construction of the center one to the two sides by a predetermined amount respectively.

9. The radiation CT apparatus according to claim 8, wherein said screen display means for changing the rotation axis coordinates displays said three tomograms, together with the coordinates of the projected rotation axis used for the respective arithmetic operations.

10. The radiation CT apparatus according to claim 8, wherein it is possible to change the settings for said predetermined amount in terms of shifting the projection coordinates of said rotation axis.

11. The radiation CT apparatus according to claim 8, further comprising an image evaluation arithmetic operation means configured to find an evaluation value concerning the definition of each image through an arithmetic operation in terms of said three tomograms, and wherein said screen display means for changing the rotation axis coordinates is configured to display the evaluation values gained through arithmetic operations together with the respective tomograms.

12. The radiation CT apparatus according to claim 8, wherein the apparatus is configured and said instruction input means is formed so as to give an instruction when either tomogram on the two sides from among said three tomograms is clicked, and at the same time, the direction of the shifting of the coordinates is set by clicking either tomogram, left or right, of said tomograms on the two sides, and the amounts of shifting of the coordinates are respectively set in accordance with the distances of the click points on said tomograms on the two sides from the center.

* * * * *